United States Patent [19]

Toyoda et al.

[11] Patent Number: 5,596,511
[45] Date of Patent: Jan. 21, 1997

[54] COMPUTING METHOD AND APPARATUS FOR A MANY-BODY PROBLEM

[75] Inventors: Shinjiro Toyoda; Hitoshi Ikeda; Eiri Hashimoto; Nobuaki Miyakawa, all of Kanagawa, Japan

[73] Assignee: Fuji Xerox Co., Ltd., Tokyo, Japan

[21] Appl. No.: 186,029

[22] Filed: Jan. 25, 1994

[30] Foreign Application Priority Data

Jan. 27, 1993 [JP] Japan ............................ 5-012032
Jan. 28, 1993 [JP] Japan ............................ 5-012908
Jan. 28, 1993 [JP] Japan ............................ 5-012909

[51] Int. Cl.$^6$ .................................................. G06F 17/00
[52] U.S. Cl. ...................................................... 364/527
[58] Field of Search ................................. 364/524, 496, 364/807, 808, 809, 527; 395/800

[56] References Cited

U.S. PATENT DOCUMENTS 4,908,781  3/1990  Levinthal et al. .................... 364/524

OTHER PUBLICATIONS

"FASTRUN: A Special Purpose, Hardwired Computer for Molecular Simulation", Richard Fine et al., PROTEINS: Structure, Function, and Genetics 11:242–253 (1991).

"Grape–2A: A Special Purpose Computer for Simulations of Many–Body Systems With Arbitrary Central Force", Toshikazu Ebisuzaki et al, Proceedings of the 24th Hawaii International Conference on System Sciences, vol. 1, pp. 171–180 (1992).

*Primary Examiner*—James P. Trammell
*Attorney, Agent, or Firm*—Finnegan, Henderson, Farabow, Garrett & Dunner, L.L.P.

[57] ABSTRACT

A proximal particle list including numbers of particles located within a predetermined distance from a particular particle is generated in calculating a Coulomb force acting on a particular particle or a related potential. A van der Waals force acting on the particular particle or a related potential is thereafter calculated based on only the particles included in the proximal particle list.

9 Claims, 8 Drawing Sheets

COMPUTING METHOD AND APPARATUS FOR A MANY-BODY PROBLEM

BACKGROUND OF THE INVENTION

The present invention relates to a special purpose method and apparatus for efficiently computing forces or potentials in molecular dynamics.

In molecular dynamics, behavior of a liquid, a solid or a high polymer is considered to result from movements of constituent atoms and is investigated by simulating those movements with a computer. A certain proper region is taken from an actual substance, and a model involving coordinates, masses, charges, velocities, etc. of all the atoms included in that region is constructed on a computer. For example, in the case of a system (model) including 10,000 particles, a force acting on an ith particle is a sum of forces from the other 9,999 particles. Therefore, it is necessary to perform 9,999 force calculations and add up the calculated results. Since this operation is performed for every particle, 99,990,000 calculations are required in total. Based on the force thus determined, an acceleration of each particle is calculated and then its speed and coordinates after a lapse of a very short time are calculated. If determination of a new speed and coordinates of each particle is called "one-step progress of calculation," several thousand to several tens of thousand steps of calculation need to be performed in molecular dynamics.

As is apparent from the above, in general, in a system including N particles, the amount of calculation of forces is approximately proportional to $N^2$ and the amount of calculation of speeds and coordinates is proportional to N. Therefore, the amount of calculation of forces becomes enormous for a large N, and it is difficult even for a supercomputer to conduct such calculation.

This is the reason why there are conventionally required special purpose computers for high-speed calculation of forces disclosed in: "FASTRUN: A Special Purpose, Hardwired Computer for Molecular Simulation," PTOTEINS: Structure, Function, and Genetics 11, pp. 242–253 (1991) and "GRAPE-2A: A Special Purpose Computer for Simulations of Many-Body Systems with Arbitrary Central Force," Proceedings of the 24th Hawaii International Conference on System Sciences, Vol. 1, pp. 171–180 (1992).

There are several kinds of forces which act between atoms. A van der Waals force acts between any types of atoms. If atoms have charges, a Coulomb force occurs between those atoms. If atoms are bonded to each other, there exists a bonding force that is in accordance with the bonding. Since in general the bonding force calculation is complex, it should be performed separately from the calculation of the other kinds of forces. Since only several atoms are connected to a single atom, the bonding force calculation is usually performed by a general purpose computer, not by a special purpose computer. That is, van der Waals forces and Coulomb forces are mainly calculated by a special purpose computer.

In many cases, the van der Waals force is expressed in the form of a well known L-J (Lennard-Jones) potential. This type of force $F_{LJ}$ is expressed as $$F_{LJ}=A(B^6 r^{-7}-2B^{12}r^{-13}) \quad (1)$$

where r is a distance between particles concerned and A and B are constants determined by a kind of particles. Since the powers of r are negative large values, $F_{LJ}$ steeply decreases as r increases. Therefore, a cutoff distance $r_c$ is determined in accordance with the accuracy required for the calculation of $F_{LJ}$. No calculations need to be performed for particle pairs whose r is larger than $r_c$. This is illustrated in FIG. 2, in which the inside of a spherical surface indicated by a solid line is a system to be considered. A spherical surface having a radius $r_c$ is assumed around an ith particle indicated as a solid circle, and forces from only mesh-applied particles located inside the spherical surface need to be calculated (forces from particles indicated by void circles need not be calculated). Since the number of particles located around a single particle is considered to be substantially constant independently of the number N of particles included in the system, the amount of calculation of forces is proportional to N.

In view of the above, in the above-mentioned two conventional techniques, a particle pair list is prepared on a host computer and forces are calculated with a special purpose computer using the list. However, to prepare such a list, it is necessary to calculate all the distances between the ith particle and the other particles. Further, this operation needs to be performed for every particle, the total amount of calculation is proportional to $N^2$ if the system includes N particles. In addition, since respective particles move, the particle pair list should be updated at proper time intervals. As a result, the proportion of the time for calculating the particle pair list to the total calculation time becomes not negligible as N increases.

Another subject to be considered when using the particle pair list relates to the capacity of a memory for storing the list. In the above-mentioned conventional technique (FASTRUN), the number of particle pairs is 583,267 when the number of particles included in the entire system is 2,204 and $r_c$ is 1.5 nm. If 32 bits (4 bytes) are required for the storage of one particle pair information, in this case about 2.3 megabytes are needed in total. Although the memory capacity of such an extent can be realized easily, the number of particles is on the order of 100,000 to deal with, for instance, a membrane of a living body. Further, if $r_c$ is increased to 2.8 nm to improve the calculation accuracy, in which case about 7,500 particles around a single particle should be considered, the capacity of about 1.5 gigabytes is required. It is very difficult to realize such a large capacity.

As described above, while the use of the particle pair list is convenient to calculate forces because the amount of calculation of forces is proportional to N, there exist problems that the amount of calculation to prepare the pair list is proportional to $N^2$ and that the capacity of a memory for storing the list increases in proportion to N.

Another problem arises in dealing with a Coulomb force $F_C$, which is expressed as $$F_C=CDr^{-2} \quad (2)$$

where C and D are charges of particles concerned. In this case, since the power of r is small, $F_C$ does not decreases steeply as r increases. Since the Coulomb force is a strong, long-range force, it is not proper in essence to introduce the cutoff distance $r_c$. In the above-mentioned two conventional techniques, the cutoff distance is used at the cost of the calculation accuracy.

On the other hand, since the van der Waals force and the Coulomb force are expressed by simple formulae (see Eqs. (1) and (2)), a special purpose computer can be constructed relatively easily by implementing calculation algorithms by hardware.

However, the bonding force cannot be calculated in a simple manner unlike the above case, but complex calculations need to be performed in accordance with the type and state of bonding. In a high polymer or the like, not only atoms directly bonded to a certain single atom but also atoms bonded to each directly bonded atom and farther atoms bonded to each atom that is bonded to a directly bonded atom need to be considered in the form of corrections. Since such corrections hardly processed by a special purpose computer and the number of atoms involved is several to ten odd, it is desirable to process those corrections on a general purpose computer (host computer) that controls a special purpose computer. Therefore, a certain means for separating particles to be subjected to calculations by the special purpose computer and particles to be subjected to calculations by the general purpose computer, as described below with reference to FIG. 3.

FIG. 3 schematically shows a state in which a certain substance is dissolved in water. In FIG. 3, a particle i indicated as a solid circle is an oxygen atom and mesh-applied particles j and k are hydrogen particles. These particles are bonded to each other to form a water molecule. An atom (or molecule) dissolved in water is denoted by l. A spherical surface having the atom i at its center and having a proper short radius $r_a$ can be assumed so that only the atoms j and k are located inside the spherical surface (the other atoms are located outside it). Also in the case of a high polymer, it is possible to assume, by properly selecting $r_a$, such a spherical surface as contains only the particles to be given special treatment. Further, it is in many cases proper to calculate by a host computer forces from particles that are not bonded to but very close to a particle of concern. Thus, it is very effective in the force calculation to separately calculate forces from particles inside and outside the spherical surface having the short radius $r_a$.

The above-mentioned two conventional techniques have a function of calculating forces acting between a particular particle and all the remaining particles and automatically generating, at the same time, a list of numbers of particles in close proximity to the particular particle. However, the conventional apparatuses calculate forces from the particles of close proximity according to Eqs. (1) and (2) and includes those forces in the sum of forces. As described below, this will cause a problem in the calculation accuracy.

In the conventional technique (GRAPE-2A), a force is calculated by 32-bit floating point arithmetic (single precision). In the single precision type calculation, in which the mantissa portion consists of only 23 bits, the calculation accuracy of at most 7 orders (a little more than 6 orders) can be assured in decimal notation. Since the particles in close proximity to the particular particle impart very strong forces to the latter, if such forces are included in the sum of forces a portion that does not fit in the 23-bit mantissa portion is rounded. Therefore, even if corrections are later effected by the host computer based on the proximal particle list, highly accurate calculation results are not expected, because very large numbers (which should not be calculated according to Eq. (1)) having large errors have already been included in the sum.

Such a deterioration of the calculation accuracy could be prevented even in the conventional technique (GRAPE-2A) by properly modifying it. For instance, this could be done by controlling, with the host computer, the calculations of the forces from the particles in close proximity to the particular particle so that the constant A becomes 0 (constants A and B are determined by the kind of particles). To this end, however, the host computer needs to obtain in advance the proximal particle list by a certain measure and control, based on the list, the calculations so that A becomes 0. Since the proximal particle list should be changed for a different particular particle, the above operation needs to be performed every time the particular particle is switched.

SUMMARY OF THE INVENTION

An object of the present invention is to reduce a calculation time for generating a particle pair list in calculating van der Waals forces by generating a particle pair list in calculating Coulomb forces.

Another object of the invention is to provide a computing apparatus which can generate a proximal particle list while reducing a load of a host computer, and which can produce highly accurate calculation results.

A further object of the invention is to provide a computing apparatus which can reduce the capacity of a memory for storing a proximal particle list.

According to the invention, a computing apparatus for a many-body problem for calculating a force acting on a particular particle or a potential of the particular particle in a system including a plurality of particles as a sum of interactions between the particular particle and the other particles, comprises:

first coordinates storage means for storing coordinates of all the particles included in the system;

first address means for sequentially supplying an address corresponding to a particle number to the first coordinates storage means;

second coordinates storage means for storing coordinates of the particular particle;

means for calculating an interparticle distance based on coordinates output from the first coordinates storage means upon reception of the address and coordinates of the particular particle read from the second coordinates storage means;

means for storing a cutoff distance;

means for comparing the calculated interparticle distance with the cutoff distance, and for generating a write signal if the calculated interparticle distance is shorter than the cutoff distance;

particle number storage means for storing the particle number upon reception of the write signal; and second address means for supplying an address to the particle number storage means;

wherein a proximal particle list including numbers of particles located within the cutoff distance from the particular particle is generated in the particle number storage means when a Coulomb force or potential is calculated, and a van der Waals force or potential is thereafter calculated based on only the particles included in the proximal particle list.

Instead of comparing the interparticle distance with the cutoff distance, the square of the interparticle distance may be compared with the square of the cutoff distance.

Further, there may be provided a host computer capable of writing and reading data to and from the particle number storage means, for reading, from the particle number storage means, a proximal particle list which has been generated in calculating a Coulomb force or potential or a van der Waals force or potential based on all the particles, storing the proximal particle list into storage means, and again calculating a Coulomb force or potential or a van der Waals force or potential using the proximal particle list read from the storage means.

According to another aspect of the invention, a computing apparatus for a many-body problem for calculating a force acting on a particular particle or a potential of the particular particle in a system including a plurality of particles as a sum of interactions between the particular particle and the other particles, comprises:

first coordinates storage means for storing coordinates of all the particles included in the system;

first address means for sequentially supplying an address corresponding to a particle number to the first coordinates storage means;

second coordinates storage means for storing coordinates of the particular particle;

means for calculating an interparticle distance based on coordinates output from the first coordinates storage means upon reception of the address and coordinates of the particular particle read from the second coordinates storage means;

means for storing a predetermined distance;

means for comparing the calculated interparticle distance with the predetermined distance, and for generating a write signal if the calculated interparticle distance is shorter than the predetermined distance;

particle number storage means for storing the particle number upon reception of the write signal;

second address means for supplying an address to the particle number storage means; and means for calculating a force or potential between the particular particle and a particle having the particle number based on the interparticle distance when not receiving the write signal, and unconditionally makes the force or potential zero when receiving the write signal;

whereby the force acting on the particular particle or the potential of the particular particle is calculated based on only particles located out of the predetermined distance from the particular particle, and a proximal particle list is generated in the particle number storage means based on particles located within the predetermined distance from the particular particle.

Instead of comparing the interparticle distance with the predetermined distance, the square of the interparticle distance may be compared with the square of the predetermined distance.

DESCRIPTION OF THE PREFERRED EMBODIMENTS

Embodiments of the present invention will be hereinafter described with reference to the accompanying drawings.

Figure 1:
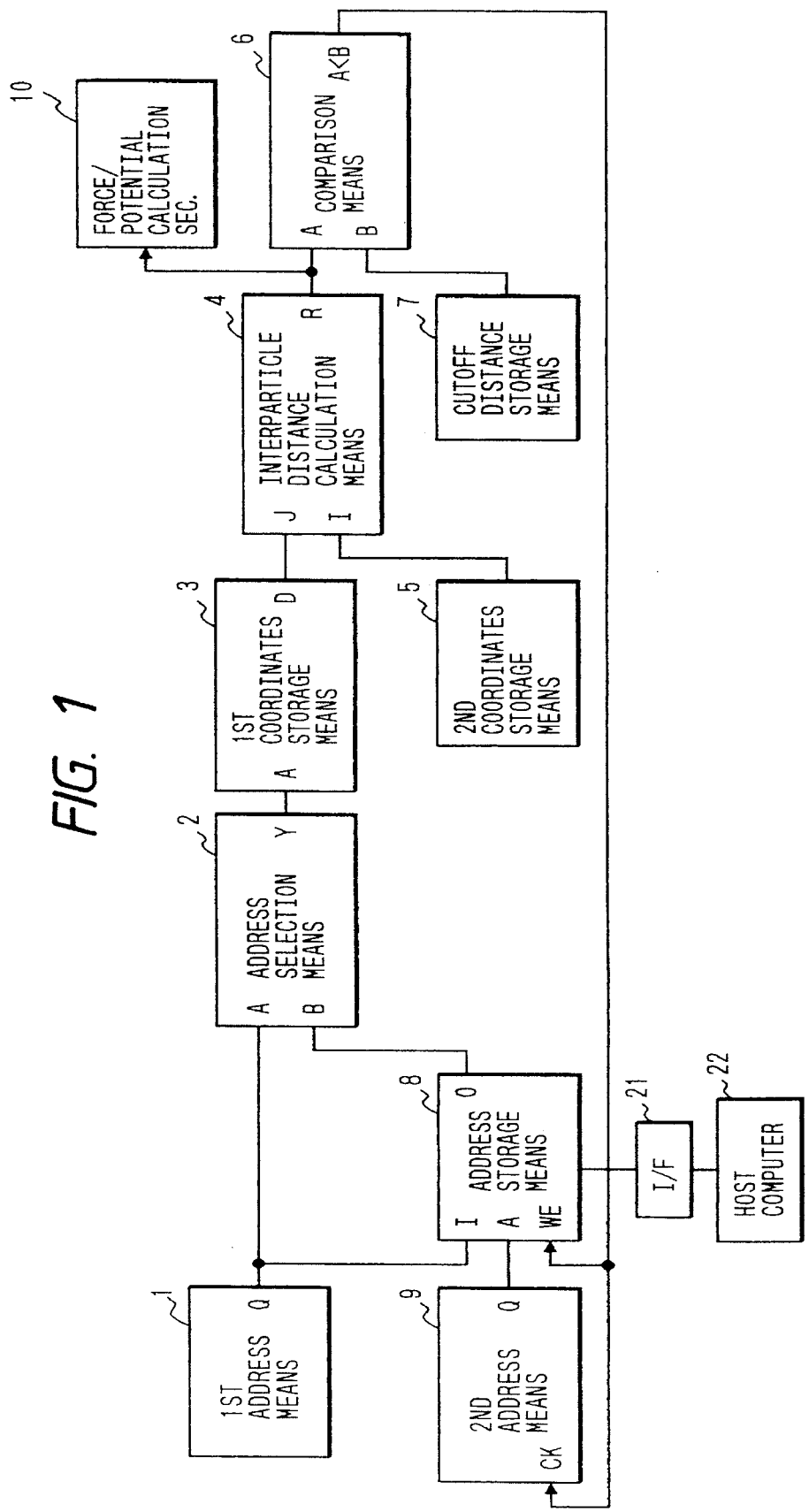
FIG. 1 is a block diagram showing constitution of a computing apparatus according to a first embodiment of the present invention.

FIG. 1 is a block diagram showing a computing apparatus for a many-body problem according to an embodiment of the invention. In FIG. 1, the computing apparatus includes a first address means 1 for designating an address of a first coordinates storage means 3; an address selection means 2 for selecting between the address from the first address means 1 and an address from an address storage means 8; the first coordinates storage means 3 for storing coordinates of particles in a system; an interparticle distance calculation means 4 for calculating distances between the particles; a second coordinates storage means 5 for storing coordinates of a particular particle, i.e., a particle i; a comparison means 6 for comparing the interparticle distances with the cutoff distance; a cutoff distance storage means 7; the address storage means 8 for storing numbers of particles located within the cutoff distance from the particular particle; and a second address means 9 for designating an address of the address storage means 8. The first address means 1 is constituted of, for instance, a down counter whose address is decremented by one for each clock pulse. The second address means 9 is constituted of, for instance, an up/down-counter whose address is incremented or decremented by one for each clock pulse.

In the computing apparatus shown in FIG. 1, forces acting between the particle i and the other particles are calculated first. In this embodiment, Coulomb forces are calculated first and then van der Waals forces are calculated.

It is assumed that coordinates $(x_i, y_i, z_i)$ of the particle 1 have been stored into the second coordinates storage means 5 in advance by a device not shown in FIG. 1, that coordinates of all of the remaining particles have been stored into the first coordinates storage means 3 in advance by a device not shown in FIG. 1, and that the cutoff distance $r_c$ for van der Waals forces has been stored into the cutoff distance storage means 7 in advance by a device not shown in FIG. 1. Number j (maximum particle number) of a first particle has been set in the first address means 1 by a device not shown in FIG. 1. The second address means 9 has been set so as to operate as an up-counter with number 0 set therein by a device not shown in FIG. 1. The address selection means 2 is set so as to select an A-input.

Upon the start of a computing operation, the number of the first particle is sent from the first address means 1 to an address-input of the first coordinates storage means 3 via the address selection means 2. As a result, coordinates $(x_j, y_j, z_j)$ of the first particle are read from the first address storage means 3 and sent to the interparticle distance calculation means 4. The interparticle distance calculation means 4 calculates an interparticle distance $r_j$ according to $$r_j = \{(x_j-x_i)^2+(y_j-y_i)^2+(z_j-z_i)^2\}^{1/2}.$$

The thus-calculated distance $r_j$ is sent to a force/potential calculation section 10 and to the comparison means 6. Based on $r_j$, the calculation section 10 calculates a Coulomb force $F_C$, a Coulomb potential, etc. Since the calculation of the Coulomb force and Coulomb potential does not directly relate to the invention, it is not explained here. The comparison means 6 compares $r_j$ with the cutoff distance $r_c$ sent from the cutoff distance storage means 7. If $r_j$ is smaller than $r_c$, the comparison means 6 activates its output to thereby send a write signal to a write terminal WE of the address storage means 8, which stores the particle number sent from the first address means 1 at its address designated by the second address means 9, i.e., address 0. Then, the comparison means 6 sends a clock signal to a clock terminal CK of the second address means 9 to increase by one the address of the second address means 9.

After completion of the processing for the first particle, the address of the first address means 1 is decremented by one to start processing for the next particle. In this manner, all the particles are processed.

When all the particles have been processed, all numbers of particles within the distance $r_c$ from the particle i should be stored in the address storage means 8. In this state, the address of the second address means 9 is an address of the final data writing plus one.

Next, van der Waals forces are calculated using the numbers of the particles located within the distance $r_c$ from the particle i, which numbers are stored in the address storage means 8. The address selection means is switched by a device not shown in FIG. 1 so as to select a B-input. The output of the comparison means 6 is always kept inactive by a device not shown in FIG. 1. The second address means 9 is set by a device not shown in FIG. 1 so as to operate as a down converter.

Upon the restart of the computing operation, the address of the second address means 9 is decremented by one to output the address that was last written to the address storage means 8. Therefore, the last number n of the particle located within the cutoff distance $r_c$ is read from the address storage means 8 and sent to the first coordinates storage means 3. Coordinates $(x_n, y_n, z_n)$ of the last-numbered particle are read from the first coordinates storage means 3 and sent to the interparticle distance calculation means 4. The interparticle distance calculation means 4 calculates an interparticle distance $r_n$, which is sent to the force/potential calculation section 10. The force/potential calculation section 10 calculates a van der Waals force $F_{LJ}$, a L-J potential, etc.

After completion of the processing for the first particle, the address of the second address means 9 is decremented by one to effect processing for the next particle. In this manner, processing for each particle is repeated until the address of the second address means 9 becomes 0.

As described above, according to the first embodiment, first the Coulomb forces imparted to the particle i from the other particles are calculated and, at the same time, the latest proximal particle list is generated for the subsequent calculation of the van der Waals forces. Therefore, it is not necessary for a host computer to perform calculations for generating the proximal particle list, nor to secure a memory space for the proximal particle list.

The apparatus is constituted such that a host computer 22 can write to and read from the address storage means 8 through an interface 21. Where it is not necessary to calculate Coulomb forces, first the van der Waals forces acting between the particle i and the other particles are calculated by using the apparatus of FIG. 1 and the proximal particle list is generated. In this case, since the proximal particle list is generated by hardware dedicated to this purpose, the calculation is faster than the case of using the host computer.

Since the forces are also determined at the same time, there can be avoided a useless operation of calculating the distances only for the purpose of generate the proximal particle list. The proximal particle list thus generated is read by the host computer 22 and stored into proper memory locations of a memory, disk, etc. If the host computer 22 writes the above proximal particle list to the address storage means 8 when van der Waals forces acting on the particle i are calculated again in the next computing step, the calculation time can be reduced greatly. In this case, however, it is necessary to secure a memory space for the proximal particle list. The proximal particle list needs to be updated for every proper steps.

Where the calculation speed is important but the calculation accuracy is not required to be high, Coulomb forces may be cut off at a proper distance even in the computing apparatus of FIG. 1 as in the case of the two conventional techniques mentioned above.

Although in the above embodiment the first address means 1 serves as a down-counter and its count value decreases from the maximum particle number during the computing operation, the invention is not limited to such constitution but the same functions can be realized by using an up-counter. In the latter case, the computing operation is finished when the count value reaches the maximum count value of the counter or when the count value reaches the maximum particle number stored in a register additionally provided.

Although in the above embodiment the second address means 9 serves as an up-counter when data is written to the address storage means 8 and as a down-converter when data is read therefrom, the invention is not limited to such constitution. The same functions can be realized by using either of an up-counter and a down-counter in each of the data writing to the address storage means 8 and the data reading therefrom.

Although in the above embodiment the first coordinates storage means 3 stores the coordinates of all the particles other than the particle i, it may also store the coordinates of the particle i. In the latter case, the coordinates of the particle i may be read from the first coordinates storage means 3. Since in such a case the distance r is 0, a force or potential can be made zero by detecting the fact that the distance r is 0. The constitution of storing the coordinates of all the particles including the particle i is advantageous in that the processing on the host computer 22 is far easier.

Although in the above embodiment the distance calculation means 4 calculates the distance r, it may calculate $r^2$. Since a square-root calculation is not required, the latter constitution has an advantage that the hardware is much simplified. In this case, however, the cutoff distance storage means 7 should store $r_c^2$ instead of $r_c$. Although the function of the force/potential calculation section 10 is changed, the constitution of the invention itself remains the same.

Figure 4:
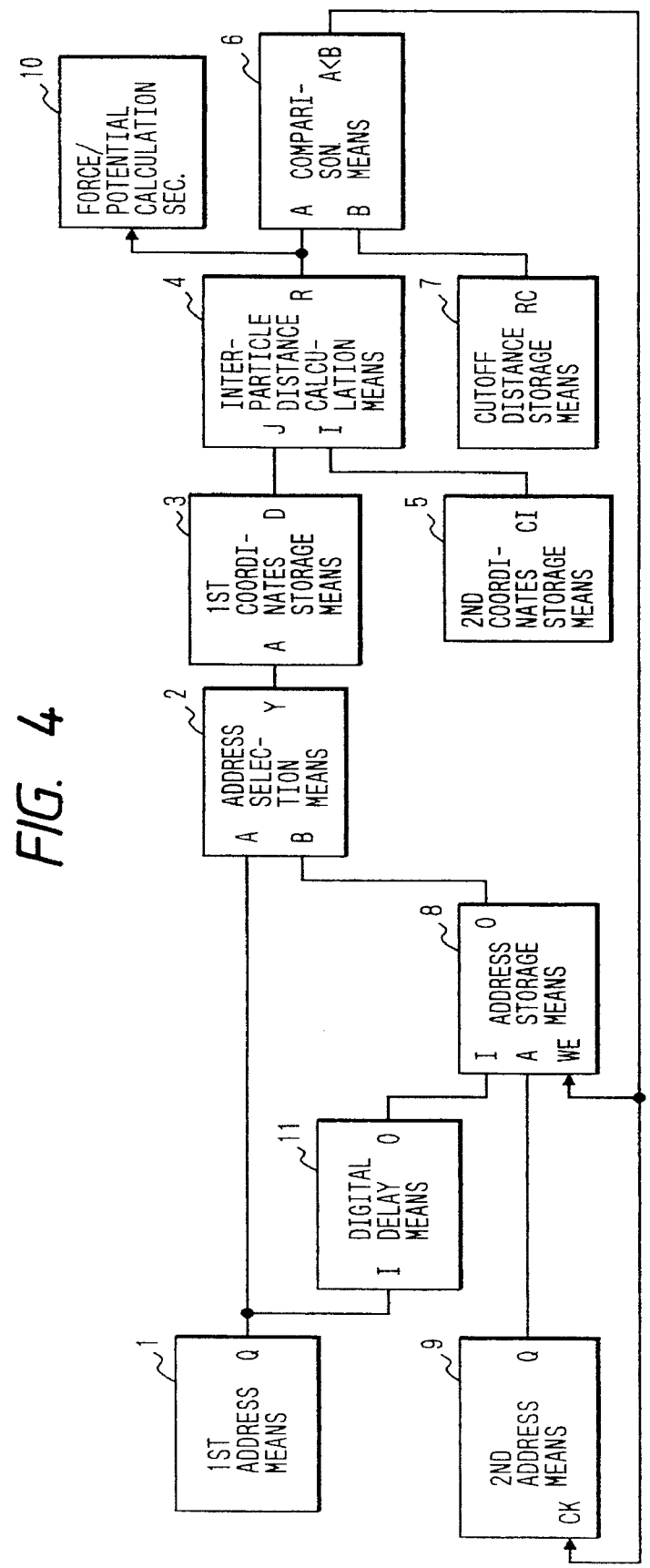
FIG. 4 is a block diagram showing constitution of a modification of the first embodiment.
Figure 5:
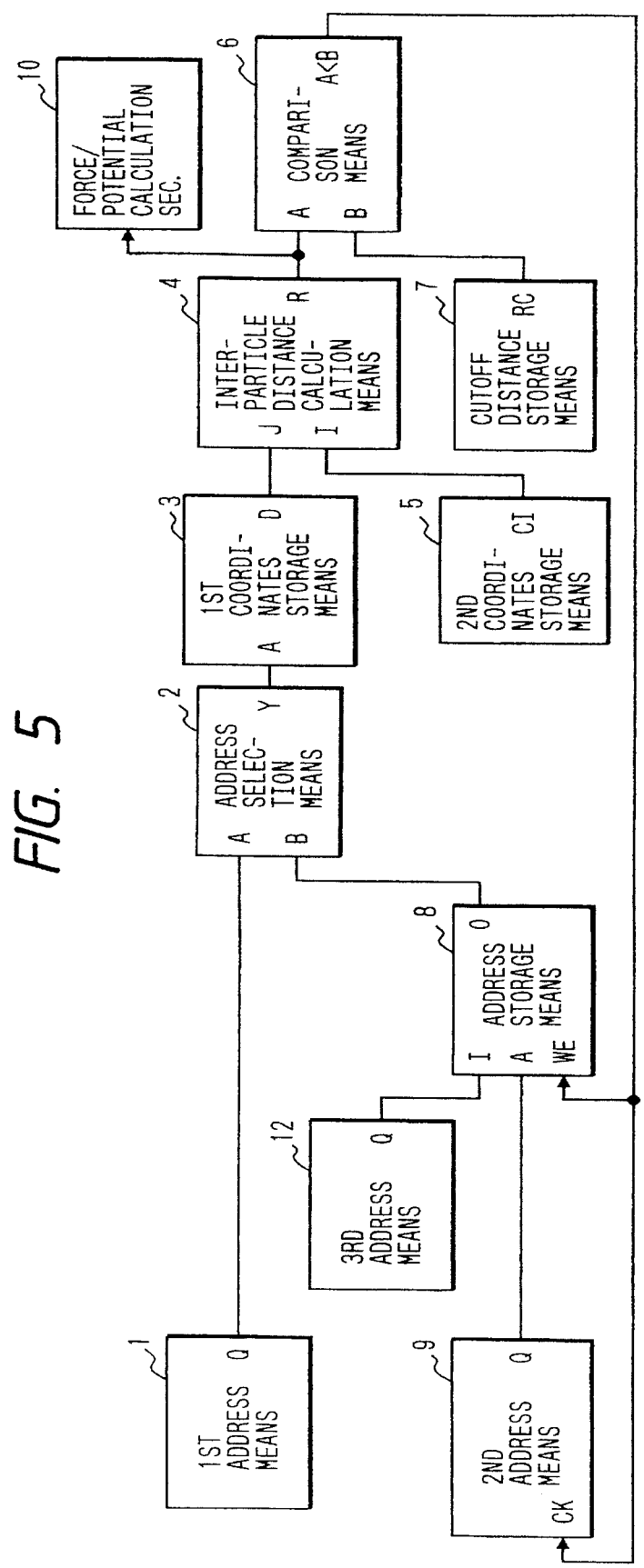
FIG. 5 is a block diagram showing constitution of another modification of the first embodiment.

Although the above embodiment has a series of operations from the address output from the first address means 1 to the address writing to the address storage means 8, these operations may be divided into plural parts to constitute a pipeline-type process. But the latter constitution is associated with a problem that when the output of the comparison means 6 is activated the output of the first address means 1 has already been changed. FIG. 4 shows a configuration to solve this problem, in which a digital delay means 11 is inserted between the first address means 1 and the address storage means 8. Alternatively, as shown in FIG. 5, a third address means 12 dedicated to the address storage means 8 may be provided to shift the address changing timing of the address storage means 8.

As described above, in the first embodiment, a list of particles located within a proper cutoff distance from a certain particle is automatically generated when Coulomb forces or potentials between the certain particle and the other particles are calculated and van der Waals forces or potentials for the certain particle are calculated based on this proximal particle list. Therefore, the calculation time of the van der Waals forces and potentials can be greatly reduced, without the need of securing a vast memory space for the proximal particle list in the host computer.

Figure 6:
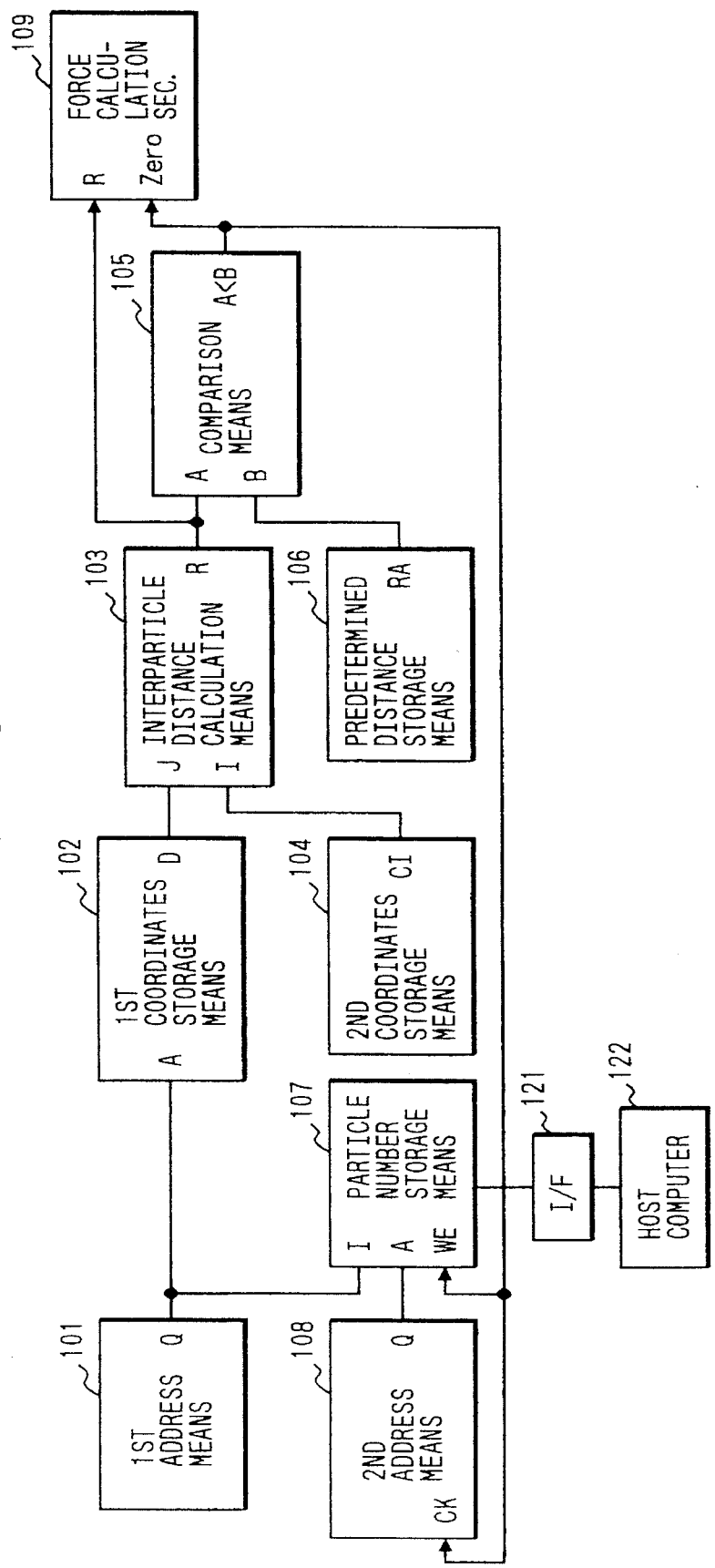
FIG. 6 is a block diagram showing constitution of a computing apparatus according to a second embodiment of the invention.

FIG. 6 is a block diagram showing constitution of a computing apparatus for a many-body problem according to a second embodiment of the invention. In FIG. 6, the computing apparatus includes a first address means 101 for designating an address corresponding to a particle address; a first coordinates storage means 102 for storing coordinates of respective particles in a system; an interparticle distance calculation means 103 for calculating distances between an particular particle and respective particles in the system; a second coordinates storage means 104 for storing coordinates of the particular particle; a comparison means 105 for comparing an interparticle distance with a predetermined distance; a storage means 106 for storing the predetermined distance; a particle number storage means 107; a second address means 108 for designating an address of the storage means 107; and a force calculation section 109. For example, the first address means 101 is a down-counter and the second address means 108 is an up-counter.

The computing apparatus of FIG. 6 calculates forces acting between a particular, ith particle and all the remaining particles. The forces may either Coulomb forces or van der Waals forces.

Figure 3:
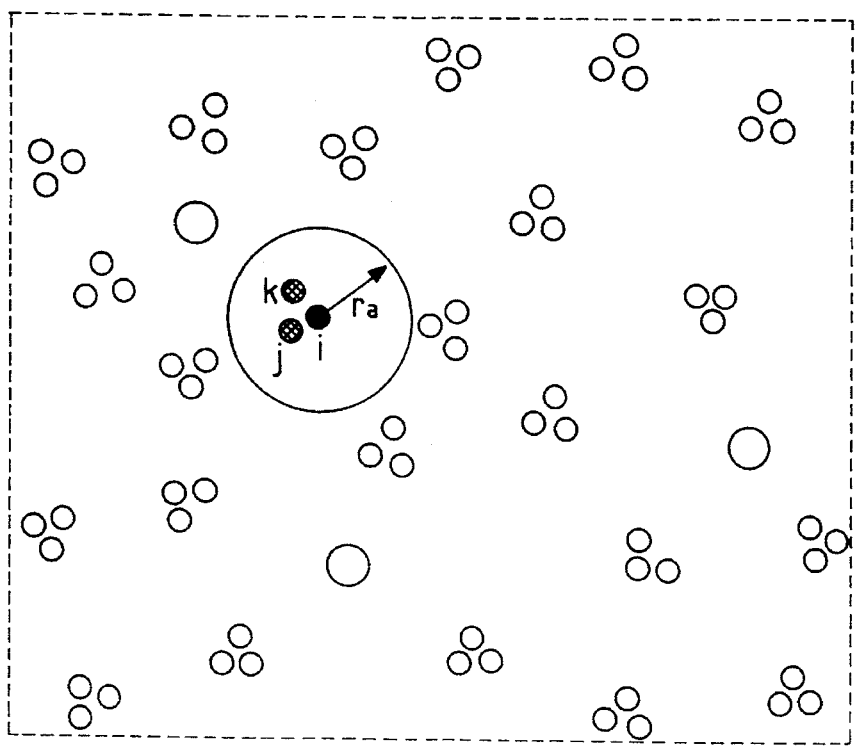
FIG. 3 illustrates a short distance that is introduced to separate particles bonded to a particle of concern from other particles.

It is assumed that coordinates $(x_i, y_i, z_i)$ of the particle i (see FIG. 3) have been stored in advance into the second coordinates storage means 104 by a device not shown in FIG. 6, that coordinates of all the particles including the particle i have been stored in advance into the first coordinate storage means 102 by a device not shown in FIG. 6, and that a predetermined distance $r_a$ has been stored in advance into the storage means 106. For example, as shown in FIG. 3, the predetermined distance $r_a$ is determined such that when the particle i (oxygen atom) is selected as the particular particle, the spherical surface defined by the radius $r_a$ contains particles j and k (hydrogen atoms) that are bonded to the particle i and does not contain particles not bonded to the particle i. It is assumed that the number j of the first particle (i.e., maximum particle number) has been set in the first address means 101 by a device not shown in FIG. 6, and that number 0 has been set in the second address means 108 by a device not shown in FIG. 6.

Upon the start of the computing operation, the number of the first particle is sent from the first address means 101 to the first coordinates storage means 102. In response, coordinates $(x_j, y_j, z_j)$ of the first particle are read from the first coordinates storage means 102 and sent to the interparticle distance calculation means 103, which calculates an interparticle distance $r_j$ according to $$r_j = \{(x_j-x_i)^2+(y_j-y_i)^2+(z_j-z_i)^2\}^{1/2}.$$

The distance $r_j$ thus calculated is sent to the force calculation section 109 and the comparison means 105. The comparison means 105 compares $r_j$ with the distance $r_a$ sent from the storage means 106. If $r_j$ is smaller than $r_a$, the comparison means 105 makes its output a high level H and stores the particle number into the particle number storage means 107. Then, the comparison means 105 increments by one the address of the second address means 108. The force calculation means 109 unconditionally makes a force zero if it receives a high-level signal H at its zero-input, while it calculates a force based on $r_j$ if it receives a low-level signal L.

After completion of the processing for the first particle, the address of the first address means 101 is decremented by one to effect processing for the next particle. In this manner, all the particles are processed. When the processing for all the particles has been finished, the numbers of particles located within the distance $r_a$ from the particle i should be stored in the particle number storage means 107. In this state, the address of the second address means 108 is the address of the last data writing plus one. Therefore, a host computer 122 can obtain a proximal particle list by reading the addresses from the second address means 108 and then reading contents of the particle number storage means 107 based on the thus-readout particle numbers through an interface 121. Forces from the particles of the list are not included in the sum of forces calculated above. Highly accurate calculation results can be finally obtained by calculating those forces on the host computer 122. The host computer disregards the existence of the particle i in the proximal particle list.

As described above, according to the second embodiment, the influences on the particle i of the particles in close proximity of the particle i are automatically regarded as 0, and the list of those particles is generated automatically. Therefore, the forces can be calculated at high speed with high accuracy.

Although in the above embodiment the first address means 101 serves as a down-counter and its count value decreases from the maximum particle number during the computing operation, the invention is not limited to such constitution but the same functions can be realized by using an up-counter. In the latter case, the computing operation is finished when the count value reaches the maximum count value of the counter or when the count value reaches the maximum particle number stored in a register additionally provided.

Although in the above embodiment the second address means 108 serves as an up-counter when data is written to the particle number storage means 107, the invention is not limited to such constitution. The same functions can be realized also by using a down-counter.

Although in the above embodiment the distance calculation means 103 calculates the distance r, it may calculate $r^2$. Since a square-root calculation is not required, the latter constitution has an advantage that the hardware is much simplified. In this case, however, the predetermined distance storage means 106 should store $r_c^2$ instead of $r_c$. Although the calculation of the force calculation section 109 is changed because of a change of its input, the constitution of the invention itself remains the same.

Although the above embodiment has a series of operations from the address output from the first address means 101 to the particle number writing to the storage means 107, these operations may be divided into plural parts to constitute a pipeline-type process. However, in the latter constitution, when the output of the comparison means 105 is activated the output of the first address means 101 has already been changed. To solve this problem, a digital delay means may be inserted between the first address means 101 and the particle number storage means 107. Alternatively, a particle number designation means dedicated to the particle number storage means 107 may be provided to shift the address changing timing of the particle number storage means 107.

Although the forces are calculated in the above embodiment, the invention is not limited to such a case but the force calculation section 9 may be replaced by a potential calculation section to calculate potentials.

As described above, in the second embodiment, the list of the particles located within the predetermined distance from a certain particle (proximal particle list) is automatically generated when the forces acting between the certain particle and the other particles are calculated, and the forces from those proximal particles are not included in the sum of forces. Therefore, the forces from the particles of the list can be calculated on the host computer, so that highly accurate calculation results can be obtained with a shorter processing time.

In the above-mentioned conventional apparatus called "GRAPE-2A," the calculations are performed using the proximal particle list by writing the coordinates of only the particles of the list to the coordinates storage means. However, when the particular particle for the force calculation is changed, the proximal particle list changes accordingly and, therefore, the contents of the coordinates storage means should be rewritten. If each of the three coordinate components x, y and z is represented by 32 bits, data of 12 bytes needs to be rewritten for one particle. If the proximal particle list includes 7,500 particles, data of 90 kilobytes in total needs to be written, which requires a vast data transfer time. In summary, the special purpose computer is effective in reducing the amount of calculation of forces by virtue of the use of the proximal particle list, the total calculation time is not much improved because extra time is needed to transfer the proximal particle list.

In the conventional computing apparatus of a many-body problem, a large-capacity memory is needed to store the proximal particle list containing a large amount of data. In producing an integrated circuit of the computing apparatus, such a large-capacity memory is hardly incorporated into a LSI and is unavoidably connected externally to the LSI. Even where the memory is externally connected to the LSI and the portions other than the memory are integrated in the LSI, a number of pins need to be extended from the LSI for connections to the memory. Further, it is necessary to consider the time for rewriting the contents of the large-capacity memory.

In view of the above, in a third embodiment of the invention described below, it is intended to enable use of a small-capacity memory for the proximal particle list by dividing an original system into a plurality of subsystems each having a low particle density and thereby reducing the number of particles to be stored as the proximal particle list of each calculation circuit.

Figure 7:
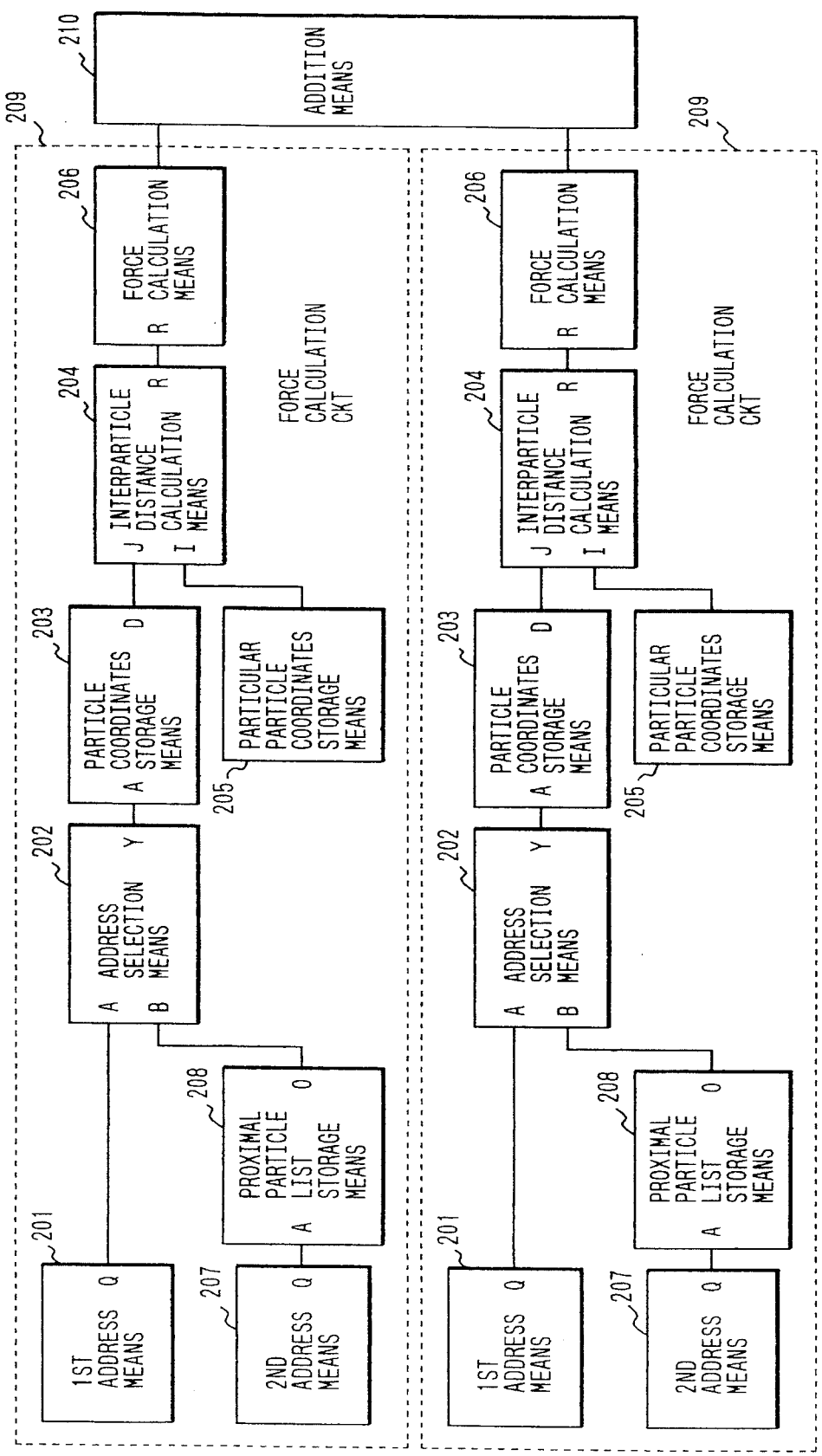
FIG. 7 is a block diagram showing constitution of a computing apparatus according to a third embodiment of the invention.

FIG. 7 is a block diagram showing constitution of a computing apparatus for a many-body problem according to the third embodiment of the invention. The computing apparatus includes two force calculation circuits 209 having the same configuration, only one of which will be described below.

The force calculation circuit 209 includes a first address means 201 for designating an address corresponding to a particle number; an address selection means 202 for selecting one of the address sent from the first address means 201 and a particle number sent from a proximal particle list storage means 208; a particle coordinates storage means 203 for storing coordinates of particles to be subjected to calculations; an interparticle distance calculation means 204 for calculating distances between the particular particle and the other respective particles; a particular particle coordinates storage means 205; a force calculation means 206 for calculating a force based on the interparticle distance calculated by the calculation means 204; a second address means 207; and the proximal particle list storage means 208 whose address is designated by the second address means 207. The forces independently calculated by the two force calculation circuits 209 are added together by an addition means 210 to finally obtain a force intended.

The operation of the one calculation circuit 209 will be described first, and then the reason of using the two calculation circuits 209 in the computing apparatus of FIG. 7 will be described. The computing apparatus of FIG. 7 can perform two calculation types to calculate forces acting on a particular, ith particle, that is, calculation types using and not using the proximal particle list.

First, the calculation type of using the proximal particle list will be described. Coordinates $(x_i, y_i, z_i)$ of the particular, ith particle have been stored in advance into the particular particle coordinates storage means 205 by a device not shown in FIG. 7, and coordinates of all the particles have been stored in advance into the particle coordinates storage means 203 by a device not shown in FIG. 7. Particle numbers 0–j are allocated to the individual particles. The first particle number j (i.e., maximum particle number) has been set in the first address means 201 by a device not shown in FIG. 7. The first address means 201 is constituted of, for instance, a down-counter, and its count value is decremented by one upon receipt of an external trigger pulse. The address selection means 202 is set so as to select its A-input, i.e., the address sent from the first address means 201. The second address means 207 and the proximal particle list storage means 208 can be set in an indeterminate state.

Upon the start of the computing operation, the first particle number j is sent from the first address means 201 to the address-input of the particle coordinates storage means 203 via the address selection means 202. Then, the first particle coordinates $(x_j, y_j, z_j)$ are read from the particle coordinates storage means 203 and sent to the interparticle distance calculation means 204. The particle number and the address are in one-to-one correspondence.

The interparticle distance calculation means 204 calculates an interparticle distance $r_j$ according to $$r_j = \{(x_j - x_i)^2 + (y_j - y_i)^2 + (z_j - z_i)^2\}^{1/2}.$$

The calculated distance $r_j$ is sent to the force calculation means 206, which calculates a force according to Eq. (1) or (2) already described above. Upon completion of the processing for the first particle, the address of the first address means 201 is decremented by one to effect processing for the next particle. In this manner, forces acting on the ith particle from all the particles are calculated.

Since the particle coordinates storage means 203 stores the coordinates of all the particles, the force from the ith particle itself is also calculated naturally. However, this force does not exist actually, and is calculated to be an infinite value, to make a calculation result meaningless. To avoid such a case, the force is unconditionally made zero when $r_j = 0$ is detected ($r_j = 0$, when j=i).

A description will be made of the case of using the proximal particle list. Numbers of particles located within the distance $r_c$ from the particle i have been stored in advance into the proximal particle list storage means 208 by a device not shown in FIG. 7, and the last address of the proximal particle list has been stored in advance into the second address means 207 by a device not shown in FIG. 7. The second address means 207 is, for instance, a down-counter, whose address is decremented by one upon every receipt of an external trigger pulse. The address selection means has been set by a device not shown in FIG. 7 so as to select the B-input, i.e., the particle number sent from the proximal particle list storage means 208.

Upon the start of the computing operation, the last address of the proximal particle list is sent from the second address means 207 to the proximal particle list storage means 208. Then, the last number n of the proximal particle list is read from the second address means 207 and given to the particle coordinates storage means 203. Particle coordinates ($x_n$, $y_n$, $z_n$) are read from the particle coordinates storage means 203 and sent to the interparticle distance calculation means 204. The interparticle distance calculation means 204 calculates a distance $r_n$. Receiving the distance $r_n$, the force calculation means 206 calculates a force. Upon completion of the processing for the last particle of the proximal particle list, the address of the second address means 207 is decremented by one to effect processing for the next particle. In this manner, forces from all the particles of the list are calculated.

In the case of using the proximal particle list, the data of the particular particle coordinates storage means 205 and the contents of the proximal particle list storage means 208 need to be rewritten when the particular particle is changed. The proximal particle list is stored in the form of particle numbers. Therefore, if each particle number is represented by 32 bits or less, the data transfer amount is 1/3 of or less than that in the case of the above-mentioned conventional technique (FASTRUN), where the coordinates x, y and z need to be rewritten. This allows the one-step calculation to be performed faster.

A description will be made of why the two force calculation circuits 209 are provided in the apparatus of FIG. 7. The calculation of forces acting on a particular particle can be performed independently of the calculations of forces acting on the other particles. Therefore, the one-step calculation time can be halved by providing the two force calculation circuits 209 to enable simultaneous calculation of forces acting on two particles. As such, basically the force calculation in molecular dynamics is suitable for a parallel computer system.

To make the entire computer smaller and less expensive in constructing a parallel computer, a computing unit needs to be as small and of a low cost as possible. To this end, it would be favorable to incorporate the entire force calculating function in a single integrated circuit. However, since the particle coordinates storage means 203 is required to store coordinates of more than 100,000 particles, the memory capacity should be more than about 1.2 megabytes. According to the present technologies, it is not practical to form, on a single chip, a circuit including such a large-capacity memory. Further considering the fact that the number of particles to be processed will increase in the future, it is appropriate to construct the particle coordinates storage means 203 in the form of an external memory.

If the maximum particle number of a processable system is about 100,000 and the maximum number of particles to be stored in the form of the proximal particle list is about 8,000, the proximal particle list storage means 208 should have a memory of 8×17 kilobits. Since the number of particles to be stored in the form of the proximal particle list is determined by the calculation accuracy, it is not conceivable that the number will much increase in the future. However, as will be apparent from the following description, the computing method of the invention becomes more effective as the number of particles in the proximal particle list increases. Even if the maximum particle number of a system to be processed is doubled, it suffices that the 17 bits mentioned above is replaced by 18 bits. With the memory capacity of such an extent, the proximal particle list storage means 208 can be incorporated into an integrated circuit. If such an memory is provided as an external memory, 32 signal terminals are required in total: 13 terminals for address lines, 17 terminals for data lines, and 1 terminal for each of chip selection and write enabling. This will cause a problem in a package of the IC. Further, the increase of the number of ICs to be mounted spoils the object of reducing the size of the entire computer.

On the other hand, in view of the cost of manufacturing ICs, it is desired that the capacity of a built-in memory be as small as possible. But a small capacity of the built-in memory may limit the number of particles of the proximal particle list, to cause a limited calculation accuracy.

Figure 2:
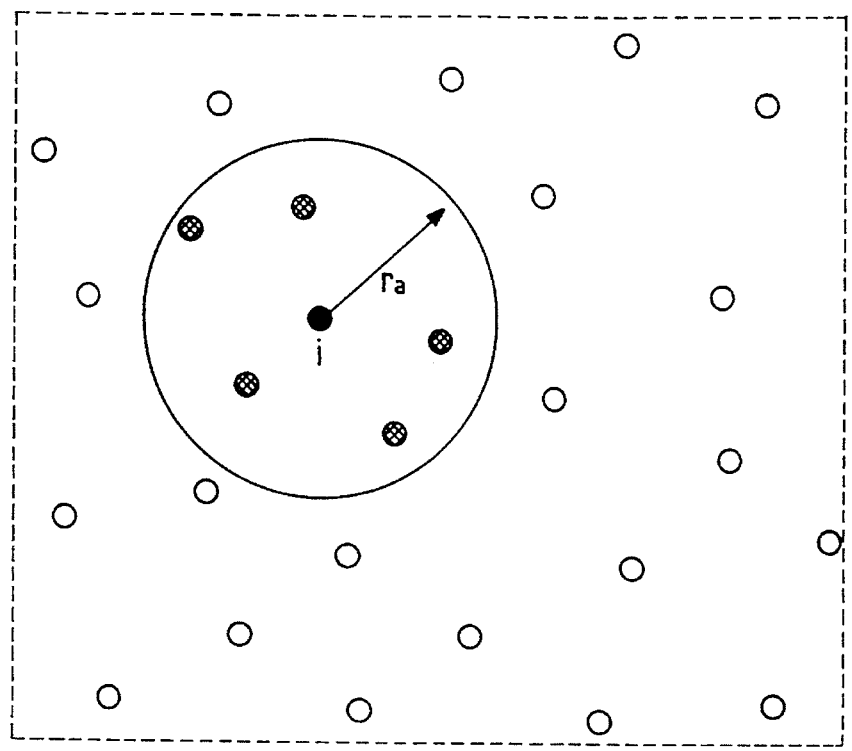
FIG. 2 illustrates a cutoff distance used in molecular dynamics.
Figure 8A:
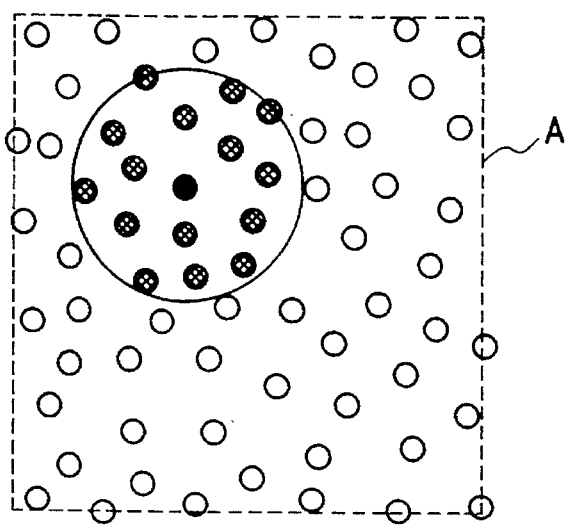
FIGS. 8(a), 8(b) and 8(c) illustrate a computing operation of the apparatus of FIG. 7.
Figure 8B:
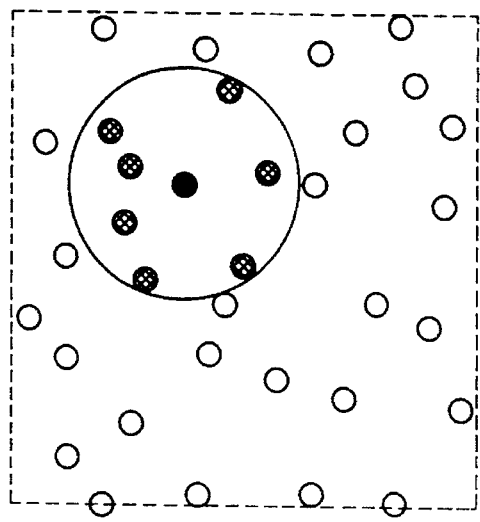
Figure 8C:
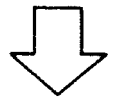
Figure 8C:
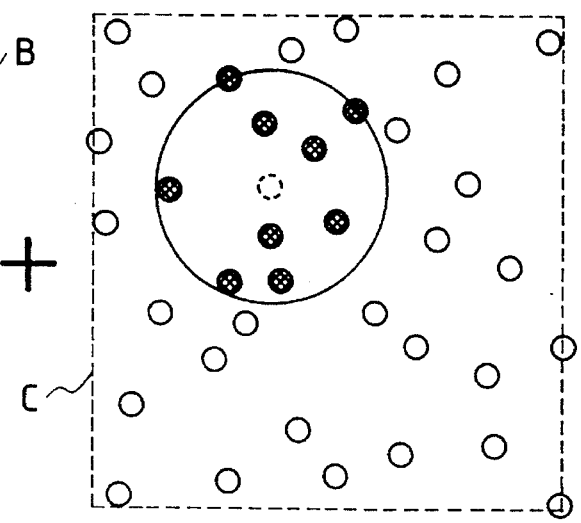

The constitution of FIG. 7 is intended to satisfy the above contradictory requirements. The computing principle of this embodiment will be described with reference to FIG. 8(a) which corresponds to FIG. 2, which was explained above. A number of particles are included in a system A indicated by a dashed line. A spherical surface having a radius $r_c$ is assumed around a particular particle indicated as a solid circle, and mesh-applied particles inside the spherical surface are included in the proximal particle list. The original system A of FIG. 8(a) is divided into two low-density systems B and C respectively shown in FIGS. 8(b) and 8(c). By properly dividing the system A (described later), the divisional systems B and C can have a particle density that is approximately a half of that of the original system A at every point of the systems, which means that the number of particles included in each of the systems B and C is also a half of that of the original system A. Importantly, this method can approximately halve the number of particles of the proximal particle list without deteriorating the calculation accuracy, because the cutoff distance $r_c$ is not changed. Since a force acting on a particular particle is a sum of forces individually imparted from proximal particles, it can be obtained by calculating the force acting on the particular particle in each of the two divisional systems and adding together the calculated forces with the addition means 210 provided in a host computer etc. That is, according to the above method in which the force is calculated by dividing the system A into the two low-density systems B and C, the memory capacity for the proximal particle list can be approximately halved. Since the embodiment of FIG. 7 has the two force calculation circuits 209, it can simultaneously process the two low-density systems B and C respectively shown in FIGS. 8(b) and 8(c).

A consideration will be made of the calculation time required in the above method of dividing the system. Since the system A is divided into the two low-density systems B and C only once at the beginning of the entire computing operation, the time for dividing the system A is negligible compared to the entire calculation time for several thousand to several tens of thousand steps. In dividing the system A into the two systems B and C, a probability that the number of particles included in the proximal particle list associated with part (b) is completely equal to that included in the proximal particle list associated with part (c) is low. Where there is a difference between the numbers of particles included in the two proximal particle lists, a time passing from the end of the calculation in connection with the proximal particle list having a smaller number of particles to the end of the calculation in connection with the proximal particle list having a larger number of particles is consumed uselessly. That is, the apparatus of FIG. 7 takes more time than the case of calculating the forces with a single force calculation circuit by the above time difference. However, by properly dividing the system A, the proportion of the useless time to the total calculation time can be reduced. In addition, if the force calculation circuits can be made smaller and mounted at a lower cost, it becomes easier to use more force calculation circuits, contributing to the reduction of the total calculation time.

Figure 9:
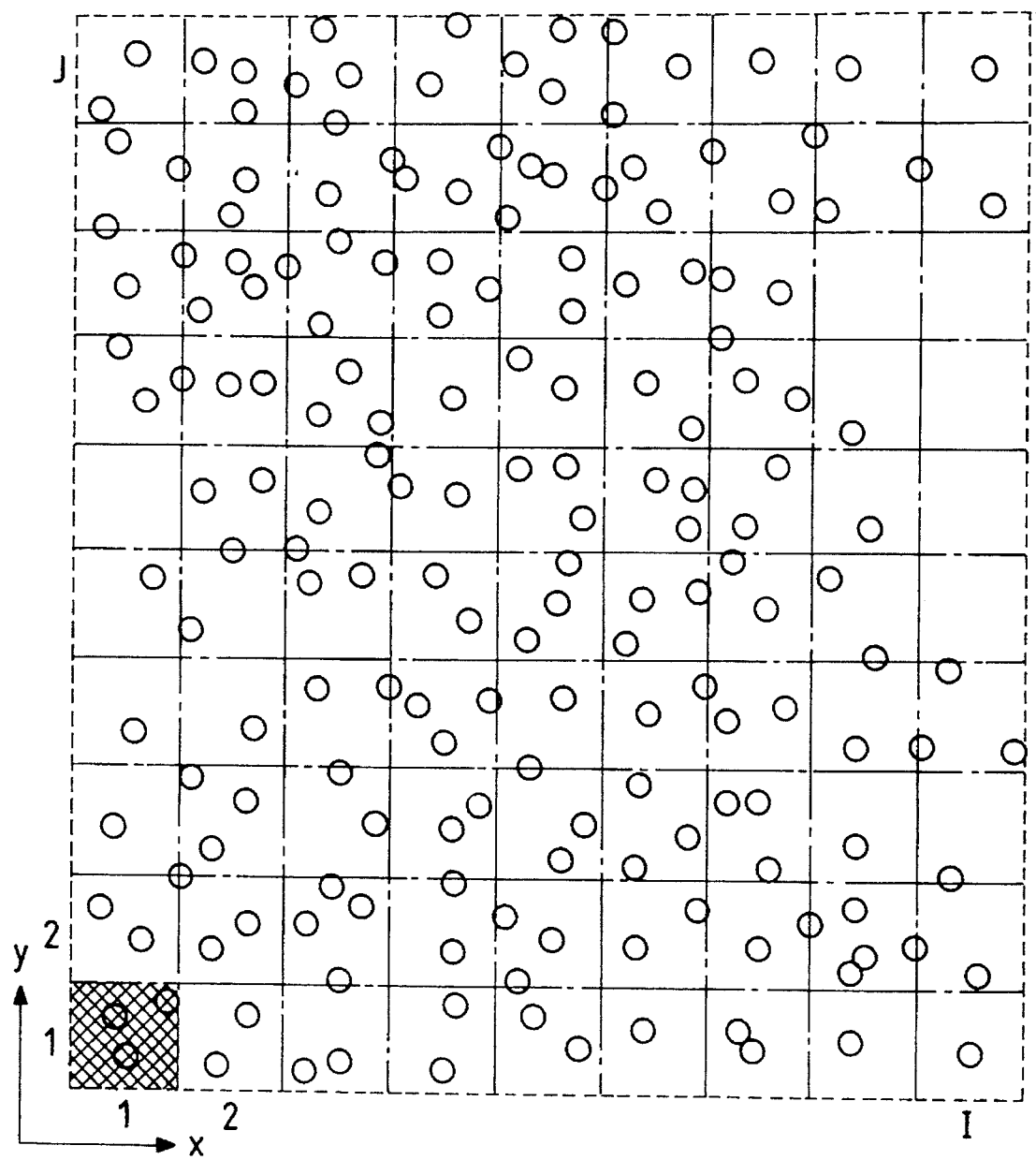
FIG. 9 illustrates how to divide an original system into two low-density systems.

Finally, a description will be made of how to divide the original system A into the two low-density systems B and C. For the convenience of description, FIG. 9 illustrates an actually three-dimensional system in a two-dimensional manner. First, the original system in equally divided into I sections in the x-direction, into J sections in the y-direction, and into K sections in the z-direction. Positive integers I, J and K are set so that each of the resulting meshes contains 1 to 20 particles. If the number of particles included in one mesh exceeds 20, i.e., the dividing number multiplied by 10, cumbersome processing is required to allocate the particles in accordance with their coordinates. The meshes obtained in the above manner are represented by D(i, j, k), where i, j and k positive integers satisfying $1 \leq i \leq I$, $1 \leq j \leq J$ and $1 \leq k \leq K$. Next, among the particles included in D(1, 1, 1) (mesh-applied portion in FIG. 9), the particle having the minimum x-coordinate is allocated to the system B and the particle having the second minimum x-coordinate is allocated to the system C. In this manner, the particles are allocated alternately in accordance with their x-coordinates. If there exist a plurality of particles having the same x-coordinate, the particle having a smaller y-coordinate is allocated first. If there exist a plurality of particles whose y-coordinates are equal to each other as well as x-coordinates, the particle having a smaller z-coordinate is allocated first. There do not exist a plurality of particles whose z-coordinates are equal to each other as well as x- and y-coordinates. Upon completion of the particle allocation for D(1, 1, 1), the particle allocation for D(2, 1, 1) is started. In this case, in D(2, 1, 1), the first particle is allocated to the system C if the last particle of D(1, 1, 1) was allocated to the system B, and vice versa. As a result of the above sequential allocation of the particles included in all the meshes to the two systems B and C, each of the two systems will have a particle density that is approximately a half of that of the original system A.

As described above, according to the above embodiment, long-range forces can be calculated without using the proximal particle list, or forces can be calculated at high speed using the proximal particle list. To improve the calculation accuracy in the case of using the proximal particle list, the proximal particle numbers can be allocated to two proximal particle lists by dividing the system to be processed into two low-density systems. Since the capacity of a memory for the proximal particle list to be incorporated in a single calculation circuit can be reduced, the single calculation circuit can be formed in an IC at a lower cost. Using a plurality of such ICs, a high speed computing apparatus dedicated to molecular dynamics can be implemented at a low cost.

Although in the above embodiment the two force calculation circuits are employed, more than two force calculation circuits may be used. If the number of calculation circuits are increased, the calculation speed can be improved accordingly.

Although in the above embodiment the original system is divided into two low-density systems in the case of using the proximal particle list, the invention is not limited to such a case. Where the proximal particle list does not fit into the proximal particle list storage means of the two calculation circuits and there exist three or more force calculation circuits, the original system may be divided into three or more low-density systems. Conversely, where the number of proximal particles is small, the original system need not be divided.

Although in the above embodiment forces acting on a particle are calculated, the invention is not limited to such a case but a potential or virial of a particle may be calculated.

Although in the above embodiment the first address means 201 serves as a down-counter and its count value decreases from the maximum particle number during the computing operation, the invention is not limited to such constitution but the same functions can be realized by using an up-counter. In the latter case, the computing operation is finished when the count value reaches the maximum count value of the counter or when the count value reaches the maximum particle number stored in a register additionally provided.

Although in the above embodiment the second address means 207 serves as a down-counter during the computing operation, the invention is not limited to such constitution. The same functions can be realized also by using a up-counter like the first address means 201.

Although in the above embodiment the distance calculation means 204 calculates the distance r, it may calculate $r^2$. Since a square-root calculation is not required, the latter constitution has an advantage that the hardware is much simplified. However, since the input of the force calculation means 206 is changed, its constitution needs to be changed accordingly.

Although the above embodiment has a series of operations from the address output from the first address means 201 or the second address means 207 to the force calculation by the force calculation means 206, these operations may be divided into plural steps to constitute a pipeline-type process.

Although in the above embodiment the original system is equally divided in each of the x-, y- and z-directions, the invention is not limited to such a case. Where the particle density is high particularly in a certain portion of the system, there does not occur any problem even if that portion is divided into smaller sections. Conversely, where the particle density is low in a certain portion of the system, that portion may be divided into larger sections. Although in the above embodiment the particle allocation starts from D(1, 1, 1), the invention is not limited to such a case but the particle allocation may start from any mesh. Although in the above embodiment the particles start to be allocated with a particle having the smallest x-coordinate, they start to be allocated with a particle having the smallest y- or x-coordinate or with a particle having the largest x-, y- or z-coordinate.

As described above, according to the third embodiment, when it is required to process a number of proximal particles to improve the calculation accuracy, a plurality of force calculation circuits are provided and the original system is divided into a plurality of low-density systems. Therefore, the number of particles included in a proximal particle list for one system can be reduced. Since the capacity of a memory for storing each proximal particle list can be reduced, the memory can be incorporated into a LSI of a force calculation circuit at a low cost. By using a plurality of such memories, a computing apparatus can be provided at a low cost which can calculate forces at high speed.

What is claimed is:

1. A computing apparatus for a many-body problem for calculating a force acting on a particular particle or a potential of the particular particle in a system including a plurality of particles as a sum of interactions between the particular particle and the other particles, comprising:

first coordinates storage means for storing coordinates of all the particles included in the system;

first address means for sequentially supplying an address corresponding to a particle number to the first coordinates storage means;

second coordinates storage means for storing coordinates of the particular particle;

means for calculating an interparticle distance based on coordinates output from the first coordinates storage means upon reception of the address and coordinates of the particular particle read from the second coordinates storage means;

means for storing a cutoff distance;

means for comparing the calculated interparticle distance with the cutoff distance, and for generating a write signal if the calculated interparticle distance is shorter than the cutoff distance;

particle number storage means for storing the particle number upon reception of the write signal; and second address means for supplying an address to the particle number storage means;

wherein a proximal particle list including numbers of particles located within the cutoff distance from the particular particle is generated in the particle number storage means when a Coulomb force or potential is calculated, and a van der Waals force or potential is thereafter calculated based on only the particles included in the proximal particle list.

2. The computing apparatus of claim 1, further comprising storage means, and a host computer capable of writing and reading data to and from the particle number storage means, for reading, from the particle number storage means, a proximal particle list which has been generated in calculating a Coulomb force or potential or a van der Waals force or potential based on all the particles, storing the proximal particle list into the storage means, and again calculating a Coulomb force or potential or a van der Waals force or potential using the proximal particle list read from the storage means.

3. A method for determining a force acting on a particle in a system including a plurality of particles, comprising the steps, executed by a data processing system, of:

generating in a particle number storage system of the data processing system, a proximal particle list including numbers of particles located within a predetermined distance from the particle; and increasing the efficiency of the data processing system by calculating a van der Waals force based on only the particles included in the proximal particle list.

4. A computing apparatus for a many-body problem for calculating a force acting on a particular particle or a potential of the particular particle in a system including a plurality of particles as a sum of interactions between the particular particle and the other particles, comprising:

first coordinates storage means for storing coordinates of all the particles included in the system;

first address means for sequentially supplying an address corresponding to a particle number to the first coordinates storage means;

second coordinates storage means for storing coordinates of the particular particle;

means for calculating an interparticle distance based on coordinates output from the first coordinates storage means upon reception of the address and coordinates of the particular particle read from the second coordinates storage means;

means for storing a predetermined distance;

means for comparing the calculated interparticle distance with the predetermined distance, and for generating a write signal if the calculated interparticle distance is shorter than the predetermined distance;

particle number storage means for storing the particle number upon reception of the write signal;

second address means for supplying an address to the particle number storage means; and means for calculating a force or potential between the particular particle and a particle having the particle number based on the interparticle distance when not receiving the write signal, and unconditionally makes the force or potential zero when receiving the write signal;

whereby the force acting on the particular particle or the potential of the particular particle is calculated based on only particles located out of the predetermined distance from the particular particle, and a proximal particle list is generated in the particle number storage means based on particles located within the predetermined distance from the particular particle.

5. The computing apparatus of claim 4, wherein the predetermined distance is set so that a spherical surface having the predetermined distance as a radius includes particles of the system other than the particular particle bonded to the particular particle but does not include particles of the system other than the particular particle not bonded to the particular particle.

6. A computing apparatus for a many-body problem for calculating a force acting on a particular particle or a potential of the particular particle in a system including N particles as a sum of interactions between the particular particle and L proximal particles in close proximity to the particular particle, where N is a positive integer not less than 2 and L is 0 or a positive integer, said apparatus comprising:

M calculation circuits, where M is a positive integer not less than 2, each of the calculation circuits comprising:

particle number storage means for storing numbers of proximal particles of about L/M;

address means for sequentially supplying an address to the particle number storage means;

particle coordinates storage means for storing coordinates of about N/M particles;

particular particle coordinates storage means for storing coordinates of the particular particle;

interparticle distance calculation means for calculating an interparticle distance based on the coordinates of the particular particle read from the particular particle coordinates storage means and coordinates read from the particle coordinates storage means in accordance with a particle number that is read from the particle number storage means in accordance with the address supplied from the address means; and means for calculating a force or potential between the particular particle and a particle corresponding to the address based on the interparticle distance; and addition means for adding together the forces acting on the particular particle or the potentials of the particular particle calculated by the M calculation circuits.

7. A computing apparatus for a many-body problem for calculating a force acting on a particular particle or a potential of the particular particle in a system including N particles as a sum of interactions between the particular particle and L proximal particles in close proximity to the particular particle, where N is a positive integer not less than 2 and L is 0 or a positive integer, said apparatus comprising:

M calculation circuits, where M is a positive integer not less than 2, each of the calculation circuits comprising:

particle number storage means for storing numbers of proximal particles of about L/M;

address means for sequentially supplying an address to the particle number storage means;

particle coordinates storage means for storing coordinates of about N/M particles;

particular particle coordinates storage means for storing coordinates of the particular particle;

distance calculation means for calculating a square of an interparticle distance based on the coordinates of the particular particle read from the particular particle coordinates storage means and coordinates read from the particle coordinates storage means in accordance with a particle number that is read from the particle number storage means in accordance with the address supplied from the address means; and means for calculating a force or potential between the particular particle and a particle corresponding to the address based on the square of the interparticle distance; and addition means for adding together the forces acting on the particular particle or the potentials of the particular particle calculated by the M calculation circuits.

8. A computing method for determining a force acting on a particle in an original system including N particles and L proximal particles in close proximity to the particle, where N is a positive integer not less than 2 and L is 0 or a positive integer, said method comprising the steps, executed by a data processing system, of:

dividing the original system into M low-density systems each having a particle density of approximately 1/M of that of the original system, where M is an integer not less than 2;

calculating a force acting on the particle or a potential of the particle in each of the M low-density systems using M calculation circuits each corresponding to a different low-density system; and summing the forces calculated by the M respective calculation circuits to obtain the force acting on the particle in the original system.

9. The method of claim 8, wherein the step of dividing the original system into the M low-density systems includes the substeps of:

dividing the original system in the x-, y- and z-directions so that each divided portion includes at most about 10×M particles, and allocating the N particles to the M low-density systems according to an order of magnitude of the x-, y- or z-coordinates of the particles.

* * * * *